(12) United States Patent
Billiet et al.

(10) Patent No.: US 9,681,881 B1
(45) Date of Patent: Jun. 20, 2017

(54) ACETABULAR REAMER

(71) Applicants: Romain Louis Billiet, Tualatin, OR (US); Hanh Thi Nguyen, Tualatin, OR (US)

(72) Inventors: Romain Louis Billiet, Tualatin, OR (US); Hanh Thi Nguyen, Tualatin, OR (US)

(73) Assignee: OURTFG CORPORATION, Beaverton, OR (US)

( * ) Notice: Subject to any disclaimer, the term of this patent is extended or adjusted under 35 U.S.C. 154(b) by 0 days.

(21) Appl. No.: 14/658,318

(22) Filed: Mar. 16, 2015

(51) Int. Cl.
| | |
|---|---|
| *A61B 17/00* | (2006.01) |
| *A61B 17/16* | (2006.01) |
| *B28B 1/24* | (2006.01) |
| *B28B 7/00* | (2006.01) |
| *B28B 7/30* | (2006.01) |
| *B28B 7/20* | (2006.01) |
| *C04B 35/64* | (2006.01) |
| *A61L 31/02* | (2006.01) |
| *A61L 31/16* | (2006.01) |
| *B22F 3/22* | (2006.01) |

(52) U.S. Cl.
CPC ........ *A61B 17/1666* (2013.01); *A61L 31/022* (2013.01); *A61L 31/026* (2013.01); *A61L 31/16* (2013.01); *B28B 1/24* (2013.01); *B28B 7/0064* (2013.01); *B28B 7/20* (2013.01); *B28B 7/303* (2013.01); *C04B 35/64* (2013.01); *A61B 2017/00526* (2013.01); *A61B 2017/00889* (2013.01); *B22F 3/225* (2013.01); *C04B 2235/945* (2013.01)

(58) Field of Classification Search
None
See application file for complete search history.

(56) References Cited

U.S. PATENT DOCUMENTS

| | | |
|---|---|---|
| 5,709,688 A | 1/1998 | Salyer |
| 6,733,703 B2 | 5/2004 | Billiet et al. |
| 7,741,254 B2 | 6/2010 | Billiet et al. |
| 8,679,124 B2 | 3/2014 | Lechot et al. |
| 8,784,422 B2 | 7/2014 | Lechot et al. |
| 2010/0155978 A1 | 6/2010 | Billiet et al. |
| 2013/0204254 A1 | 8/2013 | Slone et al. |
| 2013/0245628 A1* | 9/2013 | Sidebotham ........... A61B 17/16 606/80 |
| 2014/0296857 A1 | 10/2014 | Lechot et al. |

OTHER PUBLICATIONS

Anonymous: "420SS Bridgeback Reamers"—Tecomet, Inc. Wilmington, MA (www.tecomet.com), Symmetry Medical, Inc., Products, Symmetry Catalog, pp. 4-5 Catalog pages show sets of 45 commercial acetabular reamers in diameters ranging from 36mm to 80mm.

(Continued)

*Primary Examiner* — Sameh Boles

(57) ABSTRACT

An acetabular reamer of the type used in total hip arthroplasty (THA) to prepare a patient's acetabulum for implantation of a hip prosthesis is described. The acetabular reamer consists of a substantially hemispherical cup having a plurality of cutter-hole combinations aligned along one or more loxodromes on the surface of the hemispherical cup. The reamer, complete with integral back plate for connecting the reamer to a driver, is produced to net shape using a molding and sinterwelding technique.

18 Claims, 7 Drawing Sheets

(56) References Cited

OTHER PUBLICATIONS

Goran Augustin; Tomislav Zigman; Slavko Davila; Toma Udiliak; Tomislav Staroveski; Danko Brezac; Slaven Babic: "Cortical bone drilling and thermal osteonecrosis"—Clinical Biomechanics, vol. 27, Issue 4, pp. 313-325, May 2012 Authors claim that during bone drilling, thermal osteonecrosis will set in at temperatures above 47 degrees centigrade. This in turn will cause implant loosening.

Yutaka Shinoda; Yuki Yanagisawa; Takashi Akatsu; Fumihiro Wakai; Hidetoshi Fujii: "Development of Creep-Resistant Tungsten Carbide Copper Cemented Carbide" Materials Transactions, vol. 50, No. 6, 2009, pp. 1250-1254 Authors claim the Vickers hardness and fracture toughness of fine grained tungsten carbide copper cemented carbide were not inferior to the values for WC—Co cemented carbide.

* cited by examiner

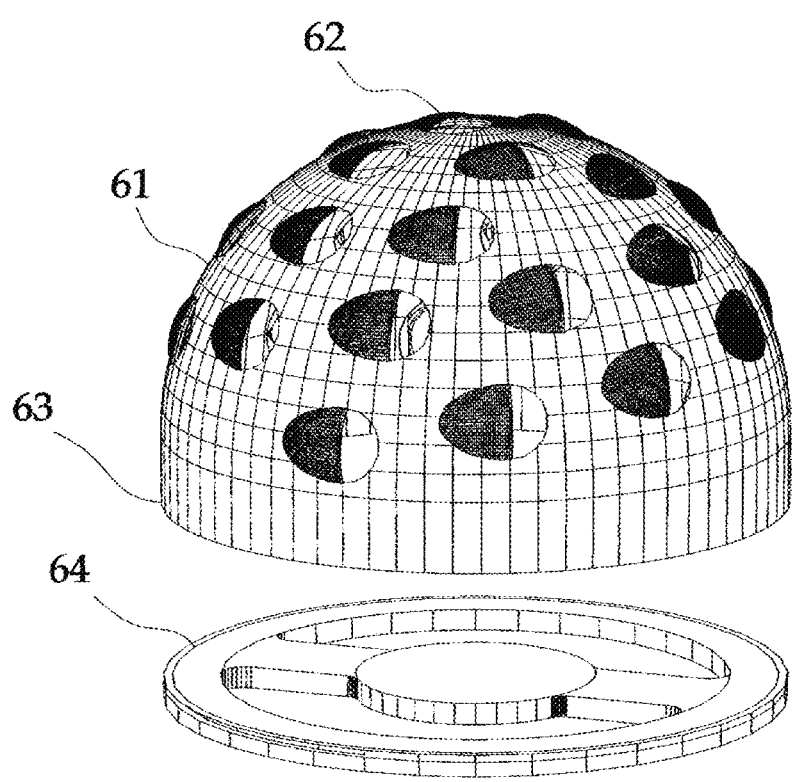

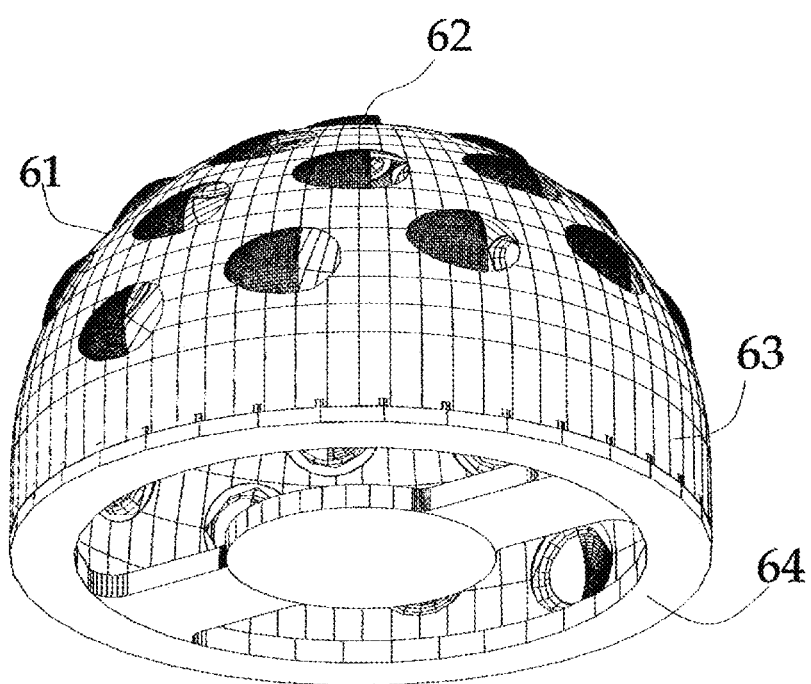

ACETABULAR REAMER

CROSS-REFERENCE TO RELATED APPLICATIONS

This application claims priority to U.S. Provisional Patent Application Ser. No. 61/972,442 filed on Mar. 31, 2014.

REFERENCES CITED

| U.S. Patent Documents | | | |
|---|---|---|---|
| 5,709,688 | January 1998 | Salyer | 601/81 |
| 8,679,124 | March 2014 | Lechot et al. | 606/80 |
| 8,784,422 | July 2014 | Lechot et al. | 606/81 |
| 7,741,254 | June 2010 | Billiet et al. | 508/100 |
| 6,733,703 | May 2004 | Billiet et al. | 264/40 |
| 2010/0155978 A1 | June 2010 | Billiet et al. | 264/16 |
| 2013/0204254 A1 | August 2013 | Slone et al. | 606/81 |
| 2013/0245628 A1 | September 2013 | Sidebotham et al. | 606/80 |
| 2014/0296857 A1 | October 2014 | Lechot et al. | 606/81 |

Foreign Patent Documents

OTHER PUBLICATIONS

"420SS Bridgeback Reamers"—Tecomet, Inc. Wilmington, Mass. www.tecomet.com), Symmetry Medical, Inc., Products, Symmetry Catalog, pages 4-5

Goran Augustin; Tomislav Zigman; Slavko Davila; Toma Udiliak; Tomislav Staroveski; Danko Brezac; Slaven Babic: "Cortical bone drilling and thermal osteonecrosis"—Clinical Biomechanics, Vol. 27, Issue 4, Pages 313-325, May 2012

Yutaka Shinoda; Yuki Yanagisawa; Takashi Akatsu; Fumihiro Wakai; Hidetoshi Fujii: "Development of Creep-Resistant Tungsten Carbide Copper Cemented Carbide"-Materials Transactions, Vol. 50, No. 6, 2009, pages 1250-1254

STATEMENT REGARDING FEDERALLY SPONSORED RESEARCH OR DEVELOPMENT

Not Applicable

REFERENCE TO A MICROFICHE APPENDIX

Not Applicable

BACKGROUND

Field of the Invention

The present invention relates to orthopedic cutting tools and, more particularly, to acetabular reamers having a domed shape for reaming a hemispherical cavity in the acetabulum.

Description of Prior Art

An acetabular reamer is a milling tool used in total hip arthroplasty (THA) to enlarge and reshape the acetabulum of the patient prior to implantation of a hip prosthesis. It typically consists of a substantially hemispherical steel cup having a plurality of cutter-hole combinations on its outer surface. The reamer is mounted axially onto the shaft of a power drill and manually pressed onto the implantation site. During rotation the cutters bite into and grate away the bone tissue of the ilium as the reamer is advanced into the acetabulum. The grated bone shavings and fragments are directed to the inner space of the reamer cup—called the debris chamber—via an ad hoc hole in front of each cutter. The accumulated bone shavings and fragments may subsequently be packed around the implanted prosthetic components to promote bone ingrowth for ensuring a tight fit between the bone and the prosthesis.

Prior art manufacturing processes for commercial, hemispherically shaped acetabular reamers are remarkably similar, usually involving some or all of following steps:

i. A thin-walled steel bowl-shaped cup blank is first fabricated by deep drawing, pressing or any equivalent method.

ii. In some cases, e.g. Salyer, U.S. Pat. No. 5,709,688, a sacrificial peripheral lip is incorporated in the design of the bowl-shaped cup blank to strengthen same and/or facilitate its handling during fabrication. When such a sacrificial peripheral lip is used, it is removed in a secondary operation before the acetabular reamer cup is completed.

iii. After deep drawing or pressing, the cup blank is perforated with a plurality of holes by punching, drilling or the like.

iv. If the holes are formed by a method that produces burs, the holes must be deburred.

v. Next, the edge of each hole is upset, countersunk or otherwise deformed outwardly to generate the cutting portion of the cutter.

vi. The cutting portion is then sharpened by sanding, grinding or the like, to yield a sharpened bevel and a cutting edge having the requisite sharpness for cutting bone.

vii. Finally, a back plate with crossbars or other system for connecting the reamer to the driver shaft is welded onto the reamer cup.

Since the cup blank is a three dimensional, substantially hemispherical shape, producing the cutters using conventional machine tools is extremely complex and difficult. For this reason, the operations of stamping, countersinking, pressing open the edges of the holes as well as sharpening the raised cutting edges are generally carried out by hand. These processes are very slow and dependent upon the skill of the individual workman. Consequently, the quality or prior art reamers is typical of manual labor.

One issue with prior art reamers is the need for the surgeon to have at his disposal a wide range of acetabular reamers in different sizes from which he can choose the most appropriate ones for a specific surgical procedure. Consequently, commercial reamers are usually supplied in sets of different sizes. One reamer manufacturer, Tecomet, Inc., Wilmington, Mass., offers sets of 45 reamers in diameters ranging from 36 to 80 mm with the number of cutters per reamer varying between 26 and 68 per reamer. Considering that each cutter-hole combination may require perforation, deburring, upsetting of the holes and sharpening of the cutter edges, it can be seen that the average number of manual operations per reamer may exceed one hundred, making the fabrication of prior art acetabular reamers labor intensive and costly.

In addition to the labor intensive manufacturing processes, there are a number of functional issues with prior art reamers.

It is highly desirable that the bone be cut into a cavity that conforms as closely as possible in shape and dimensions to the acetabular cup being implanted to avoid implant instability. Therefore, those skilled in the art have sought to provide reamers that cut a cavity that is as close as possible to a precise hemispherical shape.

It is further desirable to advance the tool linearly into the bone to fully cut the cavity, versus having to rock the tool sideways by changing its orientation to achieve a complete shape. Most commercial reamers do not incorporate cutters in the equatorial region and therefore are unable to cut a full hemispherical cavity in the acetabulum without rocking. However, this may result in overcutting of the cavity. As a result, on some commercial reamers the hemispherical shape is extended with a cylindrical skirt or rim to accommodate equatorial cutters.

Another issue with prior art reamers is the cutting speed. The hemispherical reamer rotates on its rotational axis and thus a cutter's rotational speed is an inverse function of its latitude. This results in a dilemma. First, since the cutters near the apex or pole rotate much more slowly than those near the equator, surgeons have experienced a need to apply more strength to force the reamer against the bone in the final stages of reaming. Second, the higher rotational speed of equatorial cutters may result in higher friction and therefore generate elevated temperatures. Temperatures above 47° C. cause thermal osteonecrosis which contributes to implant loosening.

Yet another issue with prior art reamers is cutter path overlap. During reaming, each cutter tends to cut a latitudinal groove in the acetabulum. As a result, to produce a smooth, substantially hemispherical cavity in the acetabulum, it is desirable for the grooves of successive cutters to overlap longitudinally. For example, in Slone, Pub. 2013/0204254, cutting blades may be positioned on the acetabular reamer so as to entirely, in other words 100% overlap, while in Salyer, U.S. Pat. No. 5,709,688, the overlap between adjacent cutting edges is about one and one half times, or 100-150%. Clearly, the higher the overlap between paths of preceding cutters, the less work will have to be expended by the cutter, thus resulting in less torque and friction. This need for overlapping is all the more important in the apex or polar region, given the slower speed in that area.

In view of the foregoing, it would be desirable if the surgeon, by selecting the correct milling cutter, could be sure that the implant seat to be milled in the bone would accommodate the acetabular cup with as close a form fit as possible and with minimal expenditure of time and energy.

It would also be desirable to provide an improved acetabular reamer having cutters that are mechanically stronger and more resistant to abrasion so that their sharpness could be maintained over an extended period of use.

It is also highly desirable to provide an improved acetabular reamer which cuts faster and requires less force to be applied against the bone.

It is also desirable to provide an improved acetabular reamer which reduces the risk of thermal osteonecrosis by being produced from a material with higher thermal conductivity and/or having a lower coefficient of friction.

It is especially desirable to provide a reaming tool which can be produced more efficiently and economically by reducing or eliminating machining operations.

Finally, it is highly desirable to provide an improved acetabular reamer and method for making same which possess all of the above desirable features.

The instant invention meets all these needs.

BRIEF SUMMARY OF THE INVENTION

According to the present invention, there is provided a method to fabricate an acetabular reamer consisting of a substantially hemispherical reamer cup incorporating an integral back plate to allow the reamer to be connected to a driver.

In the instant invention, a green body of the acetabular reamer cup without the back plate is formed in a mold. This implies two interdependent prerequisites. First, the green body must incorporate all the functional design features of the final product. Second, the green body must be ejectable from the molding tool. This latter requirement imposes restrictions on the design of the green body.

In a distinct embodiment of the instant invention, the geometry of the cutters is adapted to the mold and the design of the mold is adapted to the cutters. More specifically, each cutter geometry is achieved through a matching mold core-cavity contact.

The outer surface of the cutter is generated by an indentation or dimple in the mold cavity while the inner surface of the cutter is generated by a protrusion on the surface of the mold core. The cutter profile is specifically designed so as to not present undercuts on the outer surface of the green part except in a relatively narrow "tropical zone" defined by the particular geometry of the cutter. In this tropical zone, the undercuts are eliminated by the use of retractable radial core pins prior to mold opening.

The green reamer cup and reamer back plate are molded separately from an intimate dispersion of micrometer- or submicrometer-sized particulates of sinterable materials in an organic matrix or binder. After ejection from the mold, the green reamer cup is superposed onto the green back plate and the organic binder is extracted from the resulting assembly which is then sintered to substantially full density.

OBJECTS AND ADVANTAGES

It is a primary object of this invention to provide a method to fabricate an acetabular reamer to net shape without the need for machining and, therefore, without generating machining scrap.

It is another object of this invention to provide a method to fabricate an acetabular reamer having cutters that do not need sharpening.

Yet another object of the present invention is to provide a method to fabricate a monolithic acetabular reamer complete with back plate without the need to weld the back plate to the reamer cup.

Still another object of the present invention is to provide a method to fabricate an acetabular reamer with improved functionality over prior art reamers.

A still further object of the present invention is to provide a method to fabricate an acetabular reamer more economically than via prior art technology.

BRIEF DESCRIPTION OF THE SEVERAL VIEWS OF THE DRAWINGS

FIG. 6 shows the molded acetabular reamer comprising the reamer cup (61) with peripheral cutters (62), optional equatorial rim (63), and separately molded back plate (64).

FIG. 7 shows the completely assembled acetabular reamer in the "as-sintered" condition and comprising the reamer cup (61) with peripheral cutters (62), optional equatorial rim (63) and back plate (64).

DETAILED DESCRIPTION OF THE INVENTION

Figure 1:
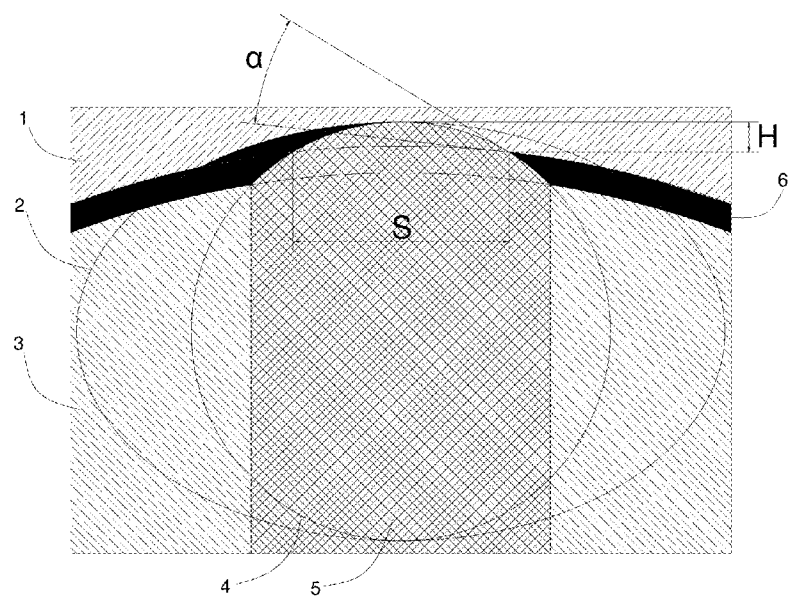
FIG. 1 is a view of a portion of a mold having a mold cavity (6) comprised between a mold cavity plate (1) and a mold core plate (3) at a point where a retractable core pin (5) in the mold core plate (3) makes contact with the mold cavity plate (1).

A novel method to fabricate an acetabular reamer of the type used in total hip arthroplasty (THA) to prepare the patient's acetabulum for implantation of a hip prosthesis is described.

The reamer of the instant invention is produced to substantially net shape by means of a molding technique, thereby circumventing the numerous, mostly manual machining operations associated with prior art acetabular reamer manufacturing.

However, typical acetabular reamer geometry is generally not amenable to molding as the cutters and adjoining holes are spread over the entire hemispherical surface of the reamer thereby generating undercuts standing in the way of part ejection from the mold.

In its simplest version, an injection mold consists of at least two halves that are fastened to the two platens of an injection molding machine. Most injection molded products are substantially cup-shaped, meaning that they have an inside and an outside surface. The outside surface of the product is formed by a cavity in the mold plate which is, therefore, termed the cavity plate, while the inside surface of the product is formed by a convex bulge or core on the mold plate which is, therefore, termed the core plate. Usually, though not always, the cavity plate is mounted on the stationary platen while the core plate is mounted on the moving platen. The reason for this is that all injection molding machines provide an ejection mechanism on the moving platen.

In the mold closed position, the void space between the cavity plate and the core plate defines the mold cavity proper into which the molding compound is injected to produce a green part. For products without undercuts, following injection and subsequent solidifying of the molding compound in the mold cavity, the mold opens when the core plate separates from the cavity plate carrying with it the green part which is subsequently stripped off the core.

If the product presents undercuts, ejection of the green part from a mold takes place in successive steps. External undercuts obstructing the free axial movement of the mold core plate must be cleared before the mold is opened. This is typically achieved by means of slides mechanically actuated by angle pins or threaded cores. When the external undercut features have been cleared, the mold can be opened by withdrawing the core plate from the cavity plate. During this motion, the green part remains on the core. Next, any internal undercuts are cleared. In the present invention this is done via retractable radial core pins. The green part can then be stripped off the core.

While radial slides and core pins are well known in the art of mold design, they are usually restricted to substantially planar sections of the mold as, for example, in molds designed to produce turbine wheels. In the acetabular reamer of the instant invention, the cutter-hole combinations are spread all over a three dimensional hemispherical surface. This would render the incorporation of slides and core pins for such design features extremely difficult if not impossible to realize. In fact, no molds for such three dimensional geometries are known in the art.

The present invention overcomes these problems by designing a reamer having cutter-hole combinations meeting the functional demands of acetabular reamers while, simultaneously, being extractable from a mold.

The acetabular reamer of the instant invention consists of a hemispherical cup, optionally extended below its equator by a cylindrical rim. The surface of the hemispherical cup is dotted with a plurality of identical cutters each one contiguous to a hole. The cutters project outwardly from the surface of the hemispherical cup such that, upon rotation of the cup about its North-South axis in the acetabulum, they tend to cut longitudinal grooves in the bone.

Referring now to the sectional view in FIG. 1, a mold has a mold cavity plate (1) and a mold core plate (3). The mold cavity plate (1) comprises a primary, substantially hemispherical cavity, optionally extended with a cylindrical rim at the hemisphere's equator. The diameter of the hemispherical cavity corresponds to the outer diameter (OD) of the green part.

The mold core plate (3) comprises a matching, concentric, convex, substantially hemispherical core, optionally extended with a cylindrical rim at the hemisphere's equator. The diameter of the hemispherical core corresponds to the inner diameter (ID) of the green part.

When the mold is closed, the void space between the mold cavity plate (1) and the mold core plate (3) defines the mold cavity proper (6).

The internal surface of the hemispherical primary cavity contains a plurality of ellipso-spheroidal secondary cavities or indentations the shape of which is obtained through the intersection of an ovoid body with the hemispherical primary cavity.

Said ovoid body consists of the union of two parts. The first part is one half of a prolate spheroid sectioned through its equatorial diameter. FIG. 1 shows the generatrix (2) of said prolate spheroid. The second part is a one half of a sphere with diameter equal to the equatorial diameter of said prolate spheroid. FIG. 1 shows the generatrix (4) of said sphere. Said half prolate spheroid and said half sphere are joined at their common equatorial diameters to form said ovoid body.

In this invention, the cutter-hole geometry is achieved through an intimate, matching contact between protrusions in the shape of identical spherical caps on the surface of the mold core and the spherical portion of the ellipso-spheroidal indentations in the primary cavity of the cavity plate. During injection, the molding compound fills the available space of the indentations. Clearly, this excludes the space of the indentation occupied by the protrusions on the mold core.

Figure 2:
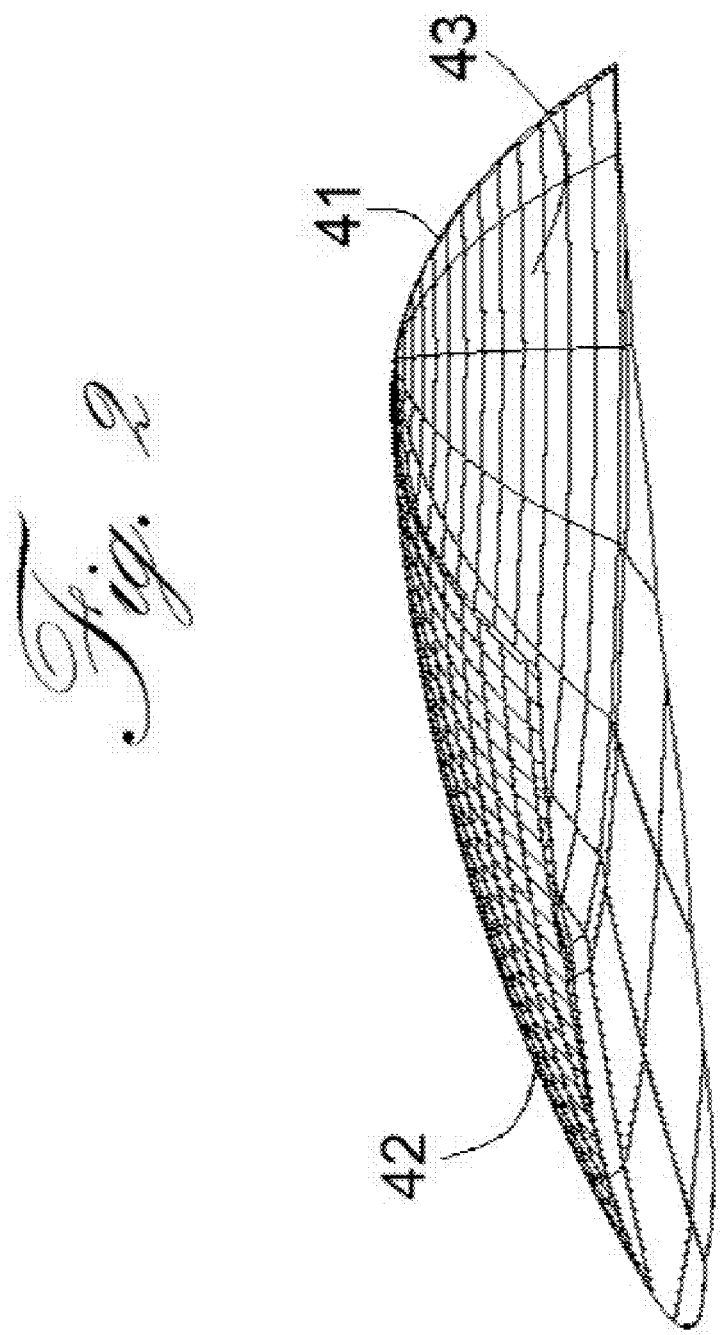
FIG. 2 is an illustration of the cutter geometry showing the cutting edge (41), the inner, spherical portion of the cutter generated by the core or retractable core pin (43) and the outer, ellipsoidal part of the cutter (42).

Referring now to FIG. 2 which is an illustration of the cutter geometry, the filled portion of the ellipso-spheroidal indentation generates the shape of the cutter (42) while the area of direct contact between the protrusion on the surface of the mold core and the ellipso-spheroidal indentation (43), being inaccessible to the flow of the molding compound, generates the underside of the cutter as well as its adjoining hole.

When the mold is closed, the identical spherical caps on the surface of the mold core intersect the hemispherical primary cavity of the mold cavity plate (1) at a constant angle of incidence (α) as shown in FIG. 1.

In this invention, the primary design parameters for the cutter-hole combination are the diameter of the hole, denoted S in FIG. 1, and the height of the cutter, denoted H in FIG. 1.

In the present design, the width of the cutter equals the diameter of the hole while the profile of the leading edge of the cutter is a circular arc with chord length S and sagitta H. The radius R of the identical spherical caps on the surface of the mold core is given by:

$$R = \frac{H}{2} + \frac{S^2}{8H}$$

If OD is the outer diameter of the hemispherical reamer cup, a sphere of radius R centered at a distance of $$\left(\frac{OD}{2} - R\right)$$

from the center of said hemispherical reamer cup will intersect same thereby defining a spherical cap with base diameter S and height H. The angle of incidence of the spherical cap with the surface of the hemispherical reamer cup, denoted α in FIG. 1, is given by:

$$\alpha = \sin^{-1}\left(\frac{4*H*S}{4H^2 + S^2}\right) - \sin^{-1}\left(\frac{S}{OD}\right)$$

The angle of incidence a defines a tropic of latitude and a corresponding tropical zone comprised between said tropic of latitude and the equator of the hemispherical reamer cup. Any cutters located at latitudes above latitude α do not present undercuts standing in the way of mold opening. Conversely, any cutters located in the tropical zone present undercuts preventing mold opening and, therefore, such undercuts must be eliminated before the mold can be opened. This is achieved by the use of retractable core pins tipped with spherical caps having base radius identical to that of the spherical caps on the mold core located at latitudes above the tropical zone.

From the dimensional analysis of prior art commercial acetabular reamers, it has been established that a typical hole diameter is about 4-5 mm while a typical cutter height is about 0.5-0.6 mm. As a practical example, for an acetabular reamer with an outer diameter (OD) of 36 mm and assuming a stainless steel molding feedstock having a shrinkage factor of 1.20275 is used, we get:

|    | Sintered dimensions, mm | Green dimensions, mm |
|----|-------------------------|----------------------|
| OD | 36                      | 43.299               |
| S  | 4.024                   | 4.84                 |
| H  | 0.56                    | 0.672                |

Using these values in above formula, we obtain α=24.62 degrees of angle. Consequently, in this example, any cutters located at latitudes higher than 24.62 degrees do not present undercuts. Conversely, any spherical caps on the surface of the mold core located between the equator and 24.62 degrees of latitude must be retracted inside the core before the mold can be opened.

The height of the cutter, denoted H in FIG. 1, and the diameter of the adjoining hole, denoted S in FIG. 1, uniquely define the width of the tropical zone. It is desirable to have a tropical zone that is as narrow as possible in order to limit the number of retractable core pins. In the example given above, the value of 24.62 degrees of angle is a compromise based on the selected practical values of the diameter of the hole S and the height of the cutter H.

Next, the geographical coordinates of the cutters and adjoining holes on the surface of the hemispherical reamer cup are accurately determined.

To maximize the number of cutters that can be accommodated onto the surface of the reamer and to ensure their even distribution, the cutter-hole combinations are aligned equidistantly along one or more substantially loxodromic paths running from the hemispherical cup's equator to near the apex or polar region. In the polar region, the loxodromic path cannot be followed precisely due to the convergence of meridians near the pole and any cutter-hole combinations in that area must be placed arbitrarily based on available space.

The longitudinal pitch in degrees of angle between successive cutter-hole combinations must take into account the angular encumbrance of the retracted core pin and the need for sufficient land between successive cutter-hole combinations. In the case of above practical example, the angular encumbrance of the retracted core pin is 23.63 degrees and an arbitrary value of 6.37 degrees was chosen as land between the end of the first equatorial cutter and the beginning of the next one in order to result in a longitudinal cutter-hole combination pitch at the equator, denoted Δ long(0), of 30 degrees. This allows for about 12 cutter-hole combinations to be placed within the tropical zone.

For reasons of symmetry, in the case of above example, two diametrically opposed loxodromes are used, each containing 6 cutter-hole combinations in the tropical zone. To maintain equal pitch between successive cutter-hole combinations arranged on a loxodrome, the longitudinal pitch must increase with increasing latitude. If Δ long(λ) is the longitudinal pitch at latitude λ, its value is given by the relation:

Δlong(Δ)=Δlong(0)/cos λ

In above example, for λ=45 degrees, we obtain Δ long (45)=42.43 degrees.

The latitudinal pitch between successive cutter-hole combinations is chosen to allow overlap in the cutting paths of successive cutters. When two or more loxodromes are used, the overlap can be one hundred percent or more.

The preferred manufacturing process for the acetabular reamer of the instant invention is the prior art technique of injection molding of metals and ceramic materials. In this technique fine metallic or ceramic particulates are homogeneously dispersed in an organic binder to yield a feedstock which is granulated and fed into the hopper of a conventional plastics injection molding machine.

Figure 4:
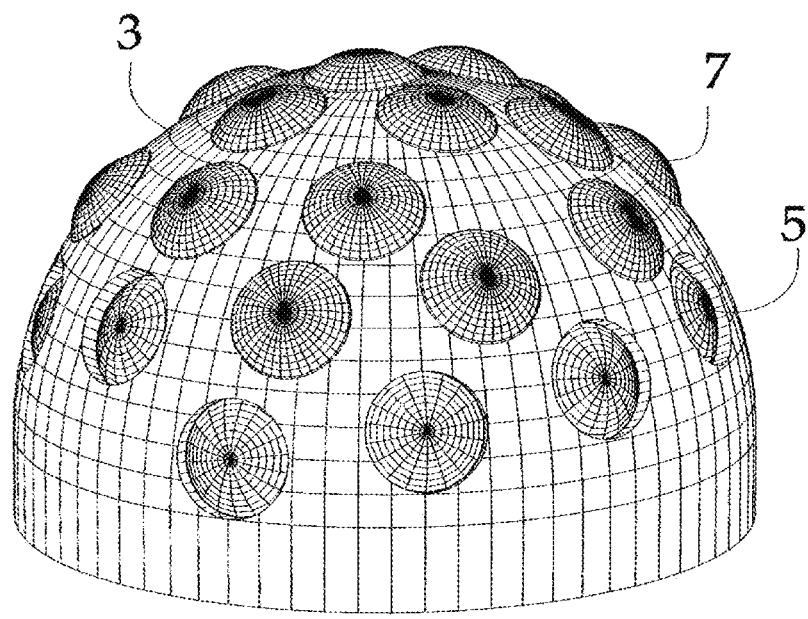
FIG. 4 shows the mold core (3) with protrusions (7) and retractable core pins (5) in the retracted position.

Molding the acetabular reamer of this invention requires the separate molding of the reamer cup, denoted (61) in FIG. 6, and the back plate, denoted (64) in FIG. 6. As the back plate (64) is an elementary shape it does not warrant elaboration. The molding sequence for the reamer cup (61) is as follows:

Step 1 The mold is open with the core pins maintained in the retracted position. FIG. 4 is a view of the mold core (3) with the retractable core pins (5) in the retracted position.

Figure 5:
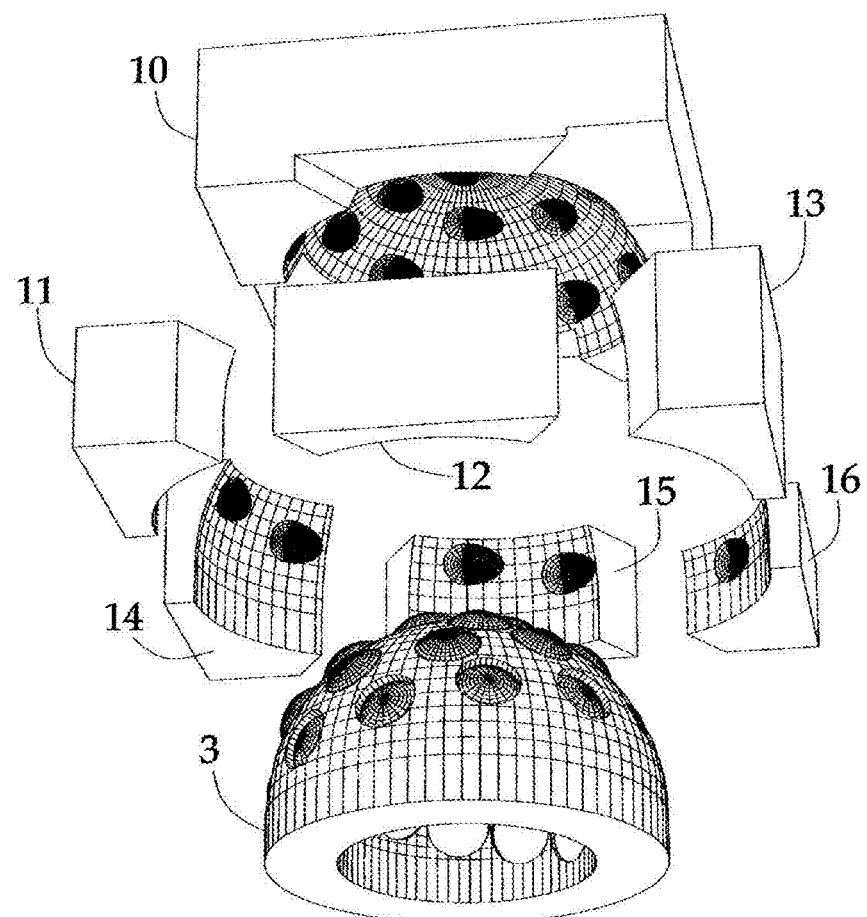
FIG. 5 is an exploded view of the mold cavity and mold core (3) showing the top of the mold cavity plate (10) and the radially extended tropical slides (11-16).

Step 2 The tropical radial slides (11-16) of the mold cavity in FIG. 5 move inward and join the top cavity (10) to seal off the mold cavity while the moving platen brings the two mold halves together in close contact.

Figure 3:
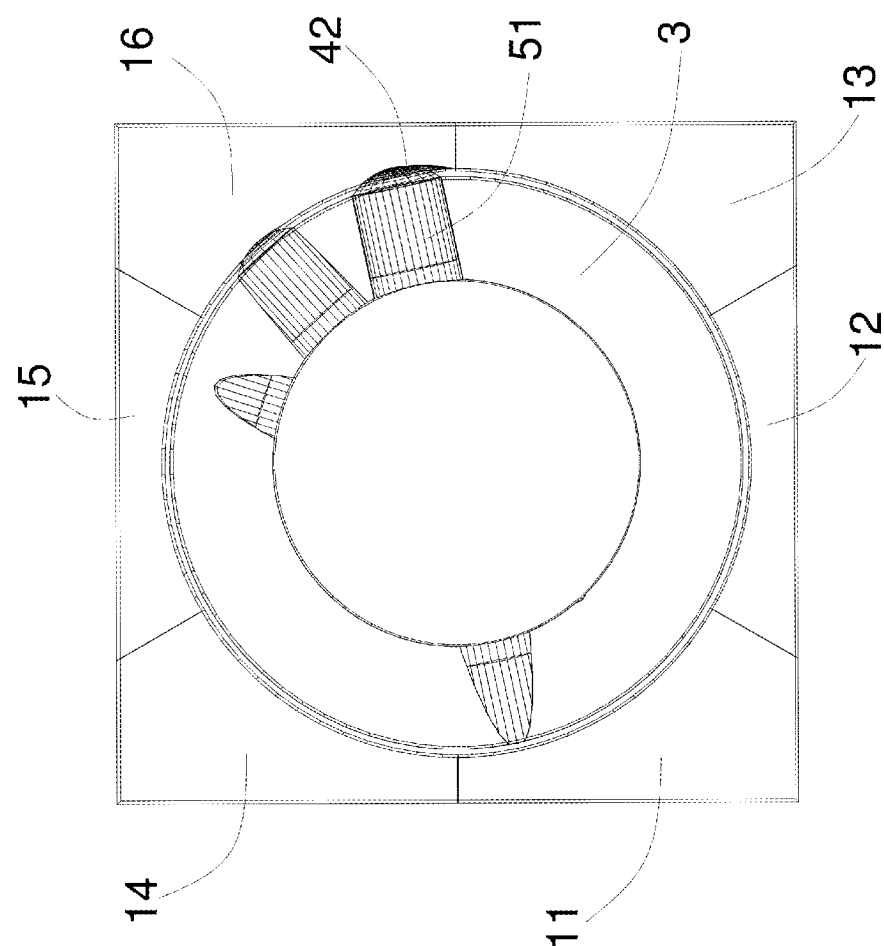
FIG. 3 shows a cross section of the closed mold along the coplanar equators of the hemispherical mold core (3) and mold cavity. The section cuts through the six tropical slides (11-16) of the mold cavity and through the equatorial core pin (51) making contact with the spherical part of the matching ellipso-spheroidal indentation in the mold cavity plate.

Step 3 The retractable core pins (5) in the mold core (3) are extended outwardly and optionally locked in place. FIG. 3 shows a cross section of the closed mold along the coplanar equators of the hemispherical mold core (3) and mold cavity. The section cuts through the tropical radial slides (11-16) of the mold cavity and through equatorial core pin (51) as it makes contact with the spherical part of the matching ellipso-spheroidal indentation in the mold cavity plate.

Step 4 The molding compound is injected into the mold cavity and allowed to freeze.

Step 5 The tropical radial slides (11-16) of the mold cavity move outward. FIG. 5 is a view of the mold cavity plate showing the radially extended tropical slides (11-16). It will be noted that since FIG. 5 is an exploded view, the raised position of the cavity top, lowered position of the core and the radial extension of the tropical slides (11-16) have been greatly exaggerated for the sake of clarity.

Step 6 The moving platen of the molding machine carrying the mold core plate (3) moves away from the fixed platen carrying the mold cavity plate (10). The green part remains on the mold core (3).

Step 7 The core pins are retracted inside the mold core (3) and the green part is stripped off the core (3).

Following molding, the organic binder is thermo-chemically extracted from the green parts and the parts are sintered to substantially full density. Appreciable volumetric shrinkage usually accompanies the sintering step.

Referring now to FIGS. 6 and 7, in a preferred embodiment of the present invention, the reamer cup (61) and the back plate, denoted (64) are molded separately from the same molding feedstock or from compatible feedstocks having the same shrinkage upon sintering. Following binder extraction, the two parts are joined by co-firing, also called sinterwelding, resulting in the integral "as-sintered" acetabular reamer shown in FIG. 7.

In another preferred embodiment, the material selected for the acetabular reamer of this invention can be any suitable stainless steel, such as the grade 420 martensitic stainless steel commonly used for commercial acetabular reamers, or it can be a ceramic material such as zirconia-toughened alumina (ZTA), or a cemented carbide such as tungsten carbide or a tungsten carbide-copper alloy which, in addition to having the hardness of tungsten carbide also has a higher thermal conductivity.

In another preferred embodiment, the cutting edge of the cutters of the acetabular reamer of the instant invention can be made razor sharp by the use of micron- or submicron-sized particulate materials in the molding feedstock.

In yet another preferred embodiment, the heat generated by friction upon rotation of the acetabular reamer can be reduced by incorporating hexagonal boron nitride particulates in the molding feedstock formulation as taught by Billiet et al., U.S. Pat. No. 7,741,254.

In another preferred embodiment, the risk of hospital acquired infection (HAI) during surgical procedures in which the acetabular reamer of the instant invention is used can be reduced by incorporating biocidal metal particulates in the molding feedstock formulation as taught by Billiet et al., US 2010/0155978 A1.

In still another preferred embodiment of the instant invention, the angle of attack, defined as the angle between the leading edge of the cutter and the cutter's meridian, can be varied.

In yet another preferred embodiment of this invention, the sintered dimensions of the acetabular reamer of the present invention can be varied by modifying the shrinkage factor upon sintering of the molding feedstock as taught by Billiet et al. U.S. Pat. No. 6,733,703.

CONCLUSION, RAMIFICATIONS AND SCOPE

In conclusion, the major advantage of this invention resides in the ability to economically produce improved acetabular reamers to net shape thus obviating the numerous, usually manual machining operations of the prior art.

Although the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

We claim as our invention:

1. A method for producing an acetabular reamer of the type having a hemispherical cup containing a plurality of cutter-hole combinations and an integral back plate for connection to a quick-release coupling mechanism, comprising the steps of:

1.1 selecting an outer diameter (OD) for the intended acetabular reamer, 1.2 selecting a hole diameter, also called base diameter (S), and cutter height (H) for the cutter-hole combinations of said acetabular reamer, 1.3 determining an angle of incidence ($\alpha$) of said cutters with the hemispherical surface of said acetabular reamer using the mathematical relation:

$$\alpha = \sin^{-1}\left(\frac{4*H*S}{4H^2+S^2}\right) - \sin^{-1}\left(\frac{S}{OD}\right)$$

where H, S and OD are as defined above, 1.4 fabricating a first injection molding tool for producing an acetabular reamer cup, comprising:

1.4.1 a mold cavity plate having a hemispherical cavity comprising:

1.4.1.1 movable radial slides in a zone between the hemisphere's equator and a parallel of latitude $\alpha$, where $\alpha$ is as defined above, and 1.4.1.2 a plurality of ellipso-spheroidal indentations distributed over substantially the entire surface of said hemispherical cavity, and 1.4.2 a mold core plate having a hemispherical mold core comprising:

1.4.2.1 a plurality of protruding spherical caps of base diameter (S) and cutter height (H) with spherical coordinates corresponding to those of the spherical part of the ellipso-spheroidal indentations in said mold cavity, and 1.4.2.2 retractable core pins in a zone between the hemisphere's equator and a parallel of latitude α, said core pins being tipped with spherical caps as defined above,
1.5 fabricating a second injection molding tool for producing a suitable back plate for connecting said acetabular reamer to a reamer driver,
1.6 providing at least one sinterable material in particulate form,
1.7 mixing said sinterable particulate material or materials with an organic binder to produce an injection molding feedstock,
1.8 molding said feedstock into green reamer cups in the first molding tool and green back plates in the second molding tool,
1.9 superposing said green reamer cups onto said green back plates to form green reamer assemblies,
1.10 extracting substantially all organic matter from said green assemblies,
1.11 sintering said binder-free assemblies to substantially full density.

2. The method of claim 1 wherein said acetabular reamer is fabricated to net shape without the need for machining.

3. The method of claim 1 wherein said acetabular reamer is fabricated to net shape without the need for welding.

4. The method of claim 1 wherein said acetabular reamer can be produced in a range of different sizes by varying said molding feedstock's shrinkage factor upon sintering and, therefore, without the need for separate tooling.

5. The method of claim 1 wherein the cutter geometry of said acetabular reamer is achieved by intimate contact between a spherical cap on the surface of said hemispherical mold core and an ellipso-spheroidal indentation in said hemispherical mold cavity.

6. The method of claim 1 wherein cutters of said acetabular reamer located at latitudes below said angle of incidence (α) are formed by intimate contact between a retractable core pin and the mold cavity.

7. The method of claim 1 wherein said cutter's leading edge forms an angle with said cutter's meridian.

8. The method of claim 1 wherein said acetabular reamer cuts a full hemispherical cavity in the acetabulum without the need for precession of the axis of rotation.

9. The method of claim 1 wherein successive cutter-hole combinations are aligned on one or more loxodromic paths on the surface of said reamer.

10. The method of claim 1 wherein said sinterable material or materials are selected from the group of metals and metal alloys, oxides, nitrides, carbides, including cemented carbides, and mixtures thereof.

11. The method of claim 1 wherein said sinterable material or materials are in micrometer- or submicrometer-sized particulate form.

12. The method of claim 1 wherein said acetabular reamer is fabricated in stainless steel.

13. The method of claim 1 wherein said acetabular reamer is fabricated in a ceramic material such as but not limited to alumina (aluminum oxide), zirconia (zirconium oxide), silicon nitride, silicon carbide or alloys thereof.

14. The method of claim 1 wherein said acetabular reamer is fabricated in cemented carbide such as but not limited to cobalt-based tungsten carbide or copper-based tungsten carbide or mixtures thereof.

15. The method of claim 1 wherein said acetabular reamer contains hexagonal boron nitride.

16. The method of claim 1 wherein said acetabular reamer contains biocidal metals.

17. The method of claim 1 wherein the physical effort the surgeon needs to exert when driving the reamer into the acetabulum is reduced.

18. The method of claim 1 wherein the risk of thermal osteonecrosis during rotation of the acetabular reamer is reduced.

* * * * *